United States Patent

Goudjil

[11] Patent Number: 5,730,961
[45] Date of Patent: Mar. 24, 1998

[54] METAMORPHIC NAIL POLISH

[76] Inventor: Kamal Goudjil, P.O. Box 1802, Boulder, Colo. 80306

[21] Appl. No.: 788,667

[22] Filed: Jan. 24, 1997

[51] Int. Cl.$^6$ .......................... A61K 7/035; A61K 7/043
[52] U.S. Cl. ........................ 424/61; 424/59; 424/401
[58] Field of Search .......................... 424/61, 59, 401

[56] References Cited

U.S. PATENT DOCUMENTS

| | | | |
|---|---|---|---|
| 5,176,905 | 1/1993 | Ohno et al. | 424/69 |
| 5,435,994 | 7/1995 | Valenty | 424/61 |
| 5,456,905 | 10/1995 | Valenty | 424/61 |
| 5,591,255 | 1/1997 | Small et al. | 106/21 A |

*Primary Examiner*—Thurman K. Page
*Assistant Examiner*—Sharon Howard

[57] ABSTRACT

A metamorphic nail polish capable of color changing from clear to any visible color (violet, red, blue, yellow . . . ) in presence of sunlight or a any ultraviolet radiation source. The nail polish will go back to colorless as soon as it is removed from the sunlight or the UV source. The present nail polish is capable of undergoing multiple reversible changes without altering its physical properties. The active chemical is a photochromic substance such as spiropyrans or spiroxazines molecules. The photochromic compound is added to any clear nail polish to form a composition sensitive to UV radiation. The composition is not toxic and does not cause skin irritation. It may be directly applied on the nail or on top of a previously applied colored enamel.

3 Claims, No Drawings

METAMORPHIC NAIL POLISH

BACKGROUND OF THE INVENTION

The present invention relates to a nail polish that has the ability of changing color from colorless to any visible color upon exposure to ultraviolet radiation for example sunlight.

Nail polish comprise a class of products regularly used by women as part of their beauty care. Enamel nail polishes are commercially available in different colors and shades. Women use this beauty accessory to match their wardrobe, jewelry and makeup. However, up to date there is no nail polish available in the market that can change color under sunlight or ultraviolet radiation and go back to colorless upon removal from ultraviolet source.

Nail polish manufacturers have focussed their work in producing a fast drying nail coat as it is shown by the numerous patents in this area, for example, U.S. Pat. No. 5,435,994 or U.S. Pat. No. 5,456,905 and the references listed therein. For instance, a photocurable nail lacquer has been developed by Rosenberg in U.S. Pat. Nos. 3,896,014 and 3,928,113. The purpose of the idea was to develop a water removable nail coat instead of the usual acetone based remover. In U.S. Pat. No. 5,435,994, Valenty describes a photoreactive nail polish coating composition that cures quickly upon exposure to low levels of ultraviolet radiation. The coating consists of a polymer formed from nitrocellulose, a photoreactive monomer, a photoinitiator, and a reaction inhibitor resulting in a product compatible with commercially available nail polish of any color. The coating is removable by commercially available acetone based polish removers. The nail polish dries in few minutes by the use of a small dose of UV radiation. In a subsequent patent, U.S. Pat. No. 5,456,905, Valenti describes a photoreactive nail polish that dries quickly upon exposure to natural light.

In U.S. Pat. No. 5,591,255, Small and Highberger teach a thermochromic ink formulation that is sensitive to temperature. In particular, they show a nail lacquer having the property of changing color with change of temperature. However, thermochromic dyes go from a color to no color therefore a color enamel has to be initially applied to produce the desired color change effect.

None of the references found show a nail polish capable of changing color from clear to any visible color upon irradiation with ultraviolet light (e.g., sunlight).

SUMMARY OF THE INVENTION

The object of the present invention is to provide a nail polish that reacts to UV radiation or sunlight by changing color from clear to any chosen color such us violet, blue, yellow, red . . . and going back to colorless form upon removed from the ultraviolet source. The present nail polish composition is able to change color reversibly by the incorporation into the composition of a photochromic substance. Photochromic substances are known in the art for their utilization in optics as storage media or as a mean to detect ultraviolet radiation for example the photochromic ultraviolet detector described in my previous patent, U.S. Pat. No. 5,581,090. Among the large family of photochromic compounds figure two groups of molecules called spiropyrans and spiroxazines. These molecules are well known for their property of photo-changing from clear to a variety of colors and shades. The spiro-compounds appear as colorless form but undergo a photochemical transformation under UV radiation to an intensely colored form. A detailed description of the chemical and physical characteristics of these compounds has been given in the U.S. Pat. No. 5,581,090.

The photochromic substance may be incorporated in different polymer matrices such as acrylics, vinyls, cellulosics, epoxies, polyesters, polystyrenes, alkyds, polyamides (nylons), polyurethanes, polycarbonates. However, in the case of nail polish nitrocellulose has been chosen because of its inherent propriety to dry faster than other polymers. Nitrocellulose lacquers are the most important of the cellulosics. They were introduced in 1920's and used as a fast drying finisher for a number of manufactured products.

Nitrocellulose Lacquers are still used by the furniture industry because of their fast drying and hand rubbing properties. Nitrocellulose is highly inflammable and explosive in dry state so it is normally delivered in a wet state, that is, moistened for example in ethanol or butanol 35% of the total weight. Other solvents carriers include: methyl acetate, ethyl acetate, n-propyl acetate, isopropyl acetate, n-butyl acetate, isobutyl acetate, ethyl propionate, acetone, methyl ethyl ketone, methyl isopropyl ketone and hydrocarbon solvents such as pentanes, hexanes.

A lacquer consisting only of a solution of nitrocellulose in a solvent gives a film which is brittle and which is completely lacking in adhesion. To improve the film properties of the lacquer plasticizers and resins are added. Plasticizers increase the flexibility of the film and reduce shrinkage on drying. Resins of various kinds are added to improve adhesion, hardness, gloss, water resistance and polishing properties. The most important plasticizers of which there is a very rich abundance are esters of phthalic. There is also a very large selection of resins which are compatible with nitrocellulose. Among the synthetic resins are alkyds, maleic resins, phenolics, urea, melamines, acrylics and vinyls.

Nitrocellulose is curable at low temperature making it a good candidate for the manufacture of nail polishes. The drying time of an enamel depends on the amount of solvent and on the nature of the solvent system. It is obvious that a solvent with high boiling point slows the drying process whereas a solvent with a lower boiling point evaporates more easily allowing a fast drying of the coating. A person skilled in the art may speed up the drying process by the incorporation of liquid monomers as solvent system. The coating material is then cured by crosslinking the monomers with polymers in the presence of catalysts.

It is not the object of this invention to give a formulation for speeding up the drying process, the description will focus on the incorporation of photochromic substances into already available formulations of clear nail polishes. The compatibility of photochromic compounds is not limited to only the existing clear nail polishes formulations but may be incorporated in any future development of formulations that are based on clear polymer resins.

In addition to the novelty feature of this invention which is changing color under ultraviolet radiation, the present metamorphic nail polish has the characteristic of acting as a filter of harmful UV rays. Indeed, spiroxazine and spiropyran molecules absorb UV radiation between 280 and 400 nm (cf., U.S. Pat. No. 5,581,090) allowing the nail coat to act as a UV block, thus protecting the nail itself from the harmful effects of UV radiation.

Since the present invention will be used on the nail of a person it is necessary to inform the public that the metamorphic nail polish does not have any toxicity and does not cause skin irritation when the photochromic compound used in this invention is imbedded in clear matrices such as commercial clear nail polish.

DESCRIPTION OF THE PREFERRED EMBODIMENTS

In accordance to the present invention, a metamorphic nail polish having the propriety of going from clear to any visible color (violet, red, blue, yellow ...) in presence of sunlight or any ultraviolet radiation source. The said nail polish will go back to colorless as soon as it is removed from the sunlight or the UV source. The present nail polish is capable of undergoing various reversible changes without altering its physical properties. The present invention will be explained below through the use of embodiments.

A spiroxazine molecule is mixed with a clear nail polish manufactured by Revlon Corp. Maximum Shine top coat from Revlon contains the following ingredients: butyl acetate, ethyl acetate, nitrocellulose, glyceryl tribenzoate, sucrose Benzoate, acrylates copolymer, isopropyl alcohol, sucrose acetate isobutyrate, etocrylene, dimethicone, acetyl tributyl citrate, FD&C yellow#5 Aluminum lake, D&C Red#7 Calcium lake, D&C Red#6 Barium lake. The spiroxazine or spiropyran compound is added in a proportion of 0.1 to 1% of the total weight of the clear nail polish. The higher the concentration of the photochromic compound the more intense is the color change.

Another clear coat where the photochromic compound can be incorporated is Top Speed manufactured by Revlon Corporation. This clear coat dries in 60 second. It contains PVB polyvinyl butyral. Another formulation of clear coat where the photochromic compound may be incorporated is Shine&Shield, from MaxFactor International, which contains the following compounds: Ethyl acetate, isopropyl alcohol, butyl acetate, propyl acetate, acrylates copolymer, dibutylphtalate, tosylamide/epoxy resin, nitrocellulose, cellulose acetate butyrate, etocrylene, benzophenone-1, keratin aminoacids, dimethicone, violet 2.

These are only few exemples and this invention isn't, in any way, limited to the above embodiments. As stressed out earlier it is possible to incorporate the photochromic compound in any polymer matrix system. Therefore, any clear nail polish that is based on a polymer resin, a solvent carrier, photocurable monomers, a photoinitiator and an inhibitor is suitable as a binder for the spiroxazines and spiropyrans molecules.

The photochromic compound is dissolved into the clear nail polish by the solvents already present in the mixture. Depending upon the substituent group incorporated in the Spiroxazine molecule the coloration may vary from red, blue, violet to yellow. It is also possible to create any color hue by mixing two or more spiroxazine or spiropyran molecules in the clear coat. However, a precaution has to be taken on the choice of the solvent system. Indeed the formulation should not contain any traces of acid since the spiroxazine and spiropyran molecules are very sensitive to acidic media. This is mainly due to the structure of the open chain merocyanine molecule resulting from the irradiation of the spiro-compound with ultraviolet light.

The obtained formulation of metamorphic nail polish is applied directly to the nail by a paint brush and allowed to air dry. Upon exposure to a UV lamp, the top coat on the nail went from clear to intensely colored within 5 seconds and then back to colorless as soon as the UV source is removed. The same experiment was performed under sunlight. The metamorphic nail polish exhibited the same reversible photo-transformation.

In addition, it is possible, as in the case of the usual clear nail polishes, to apply the present metamorphic nail polish on top of a color enamel. In this case, the metamorphic nail polish will allow the color of the nail to change from a given color (the color of the enamel) to another upon exposure to UV radiation for example sunlight.

As it has been pointed out in my earlier patent U.S. Pat. No. 5,581,090, the photochromic substance has a limited life time due to oxidation processes. The adjunction of a UV stabilizer is recommended. After performing testing on different stabilizers available in the market, Tinuvin 765 and Tinuvin 144 Hindred Amine Light Stabilizers, supplied by Ciba Geigy, Additive Division, have been selected for their performance under sunlight. The stabilizers are added in a proportion of 2.5% to 3% in weight. The Hindred Amine Light Stabilizers are incorporated in the photochromic composition so as to be in close physical proximity to the organic photochromic compounds imbedded in organic matrices (clear polymers).

What is claimed is:

1. A metamorphic nail polish comprising:
   (a) a photochromic compound corresponding to any molecule in the spiroxazine or spiropyran group, and
   (b) a composition of clear nail polish containing: a base resin consisting of a polymer such as nitrocellulose and cellulose acetate butyrate, a photoreactive monomer, organic solvents, a photoinitiator and an inhibitor;
   wherein said photochromic compound is mixed to the said clear nail polish to form a composition sensitive to UV radiation.

2. The coating of claim 1, further comprising:
   (c) an anti-oxidant consisting of ultraviolet light stabilizers such as Hindred Amine Light Stabilizers;
   wherein said anti-oxidant is used in concentration between 2.5 to 3% by weight of the total composition.

3. The nail polish of claim 1 contains means for protecting the nail from UV radiation.

* * * * *